(12) United States Patent
Lorén et al.

(10) Patent No.: US 11,959,044 B2
(45) Date of Patent: Apr. 16, 2024

(54) CONCEPT FOR THE PRODUCTION OF FOOD WITH REDUCED ENVIRONMENTAL IMPACT

(71) Applicant: Green-On AB, Gothenburg (SE)

(72) Inventors: Anders Lorén, Borås (SE); Marcus Vestergren, Borås (SE)

(73) Assignee: Green-On AB, Gothenburg (SE)

( * ) Notice: Subject to any disclaimer, the term of this patent is extended or adjusted under 35 U.S.C. 154(b) by 569 days.

(21) Appl. No.: 17/267,568

(22) PCT Filed: Aug. 14, 2019

(86) PCT No.: PCT/EP2019/071816
§ 371 (c)(1),
(2) Date: Feb. 10, 2021

(87) PCT Pub. No.: WO2020/035528
PCT Pub. Date: Feb. 20, 2020

(65) Prior Publication Data
US 2021/0324301 A1 Oct. 21, 2021

(30) Foreign Application Priority Data
Aug. 16, 2018 (SE) .................................... 1850984-4

(51) Int. Cl.
*C11C 3/02* (2006.01)
*A23K 20/158* (2016.01)
(Continued)

(52) U.S. Cl.
CPC .............. *C11C 3/02* (2013.01); *A23K 20/158* (2016.05); *A23K 50/90* (2016.05); *A23L 29/04* (2016.08);
(Continued)

(58) Field of Classification Search
CPC .......... C11C 3/02; C25B 1/04; C07C 29/151; C07C 1/20; C07C 51/23; C07C 2/04; C07C 2/24; C07C 1/0485; C07C 51/15
See application file for complete search history.

(56) References Cited

U.S. PATENT DOCUMENTS 3,676,489 A 7/1972 Ellis et al.
5,550,220 A 8/1996 Meyer et al.
(Continued)

FOREIGN PATENT DOCUMENTS

CN 107567351 A 1/2018
GB 2448685 A 10/2008
(Continued)

OTHER PUBLICATIONS

Lutz, E. F., Shell higher olefins process, Journal of Chemical Education, vol. 63, No. 3, pp. 202-203 (Year: 1986).*
(Continued)

*Primary Examiner* — Yate' K Cutliff
(74) *Attorney, Agent, or Firm* — Clark & Elbing LLP

(57) ABSTRACT

Edible organic compounds which can serve as food or feed, or as components of food or feed, are synthesized from oxidized carbon and water, through the input of energy, and using well-known and validated synthesis pathways, leading to free fatty acids and optionally esterified to triglycerides. The source of carbon is preferably $CO_2$ from the atmosphere, or more preferably point sources of $CO_2$ from industry and/or energy production.

18 Claims, 3 Drawing Sheets

(51) Int. Cl.
| | |
|---|---|
| A23K 50/90 | (2016.01) |
| A23L 29/00 | (2016.01) |
| C01B 32/40 | (2017.01) |
| C07C 1/04 | (2006.01) |
| C07C 1/20 | (2006.01) |
| C07C 2/04 | (2006.01) |
| C07C 11/04 | (2006.01) |
| C07C 31/04 | (2006.01) |
| C07C 51/23 | (2006.01) |
| C07C 51/25 | (2006.01) |
| C25B 1/04 | (2021.01) |

(52) U.S. Cl.
CPC ............ *C01B 32/40* (2017.08); *C07C 1/0485* (2013.01); *C07C 1/20* (2013.01); *C07C 2/04* (2013.01); *C07C 11/04* (2013.01); *C07C 31/04* (2013.01); *C07C 51/23* (2013.01); *C07C 51/25* (2013.01); *C25B 1/04* (2013.01); *Y02E 60/36* (2013.01)

(56) References Cited

U.S. PATENT DOCUMENTS

| | | | | |
|---|---|---|---|---|
| 6,121,502 | A | 9/2000 | Tembe et al. | |
| 6,166,282 | A * | 12/2000 | Miller ................ | C10G 11/18 585/641 |
| 8,198,338 | B2 * | 6/2012 | Shulenberger ........ | C10K 3/026 518/703 |
| 11,274,321 | B2 * | 3/2022 | Reed ..................... | C12P 7/16 |
| 2016/0281115 | A1 * | 9/2016 | Hickey ................. | C12P 7/065 |
| 2018/0086985 | A1 * | 3/2018 | von Olshausen ....... | C25B 15/02 |

FOREIGN PATENT DOCUMENTS

| | | |
|---|---|---|
| WO | WO-2016/161998 A1 | 10/2016 |
| WO | WO-2017/174048 A1 | 10/2017 |

OTHER PUBLICATIONS

Adlof et al., "Synthesis and Physical Properties of Symmetrical and Non-symmetrical Triacylglycerols Containing Two Palmitic Fatty Acids," J Am Oil Chem Soc. 85(2):99-104 (2008).

International Search Report and Written Opinion for International Application No. PCT/EP2019/071816, dated Dec. 9, 2019 (16 pages).

International Preliminary Report on Patentability for International Application No. PCT/EP2019/071816, dated Oct. 30, 2020 (16 pages).

Anning Zhou et al., Introduction to Carbon—chemical industry, pp. 111-113, China University of Mining and Technology Press (Sep. 30, 2017) (5 pages).

Hawk et al., *Practical Physiological Chemistry, Thirteenth Edition*. People's Medical Publishing House, p. 472 (Sep. 30, 1961) (3 pages).

Jiang et al., "Iron Catalysis for Room Temperature Aerobic Oxidation of Alcohols to Carboxylic Acids," manuscript available in ACS Jun. 15, 2016, published in final edited form as: J Am Chem Soc. 138(27):8344-7 (Jul. 13, 2016) (6 pages).

Office Action for Chinese Application No. 201980053100.1, dated Feb. 18, 2023 (25 pages).

Tianxiang Nie, Diet application version of eye care herb, p. 161, China Press of Traditional Chinese Medicine (Jun. 30, 2017) (3 pages).

Yiqun Jia et al., Identification of Food Additives and pharmaceutical excipients by mass spectrometry and infrared spectroscopy, p. 16, Jilin University Press (Dec. 31, 2007) (3 pages).

Zhou et al., "Synthesis of fatty alcohols from olefins using low valence zirconium compounds as Catalysts," Journal of Lanzhou University 19(4):171 (Dec. 31, 1983).

Office Action for Chinese Application No. 201980053100.1, dated Oct. 25, 2023 (21 pages).

Zhou et al., "Synthesizing fatty alcohols from olefin by using a low-valent zirconium compound as a catalyst," Journal of Lanzhou University 19(4):171 (Dec. 31, 1983).

* cited by examiner

CONCEPT FOR THE PRODUCTION OF FOOD WITH REDUCED ENVIRONMENTAL IMPACT

TECHNICAL FIELD

The present disclosure relates to the field of organic synthesis, in particular to a novel concept for producing food or feed directly from carbon dioxide, water and energy. Thus, the present invention provides methods for the synthesis of edible organic compounds which can serve as food or feed, or as components of food or feed. Ultimately this serves to minimize the need for agriculture and animal farming, and may significantly reduce and even reverse the environmental impact of the earth's growing population.

BACKGROUND

According to the report "World Population Prospects, the 2017 revision (United Nations, Department of Economic and Social Affairs, Population Division) the global human population growth amounts to around 83 million annually, or approximately 1.1% per year. The global population has grown from an estimated 1 billion in 1800 to 7.616 billion in 2018. The population is expected to keep growing, and estimates have put the total population at 8.6 billion by mid-2030, 9.8 billion by mid-2050 and 11.2 billion by 2100.

In the article "A safe operating space for humanity" in Nature 461, 472-475 (24 Sep. 2009) Johan Rockström et al. stress the importance of identifying and quantifying planetary boundaries that must not be transgressed, in order to help prevent human activities from causing unacceptable environmental change. The authors defined nine interlinked planetary boundaries, proposing a safe operating space for each, and estimating the current situation. They found that the boundaries in three systems (rate of biodiversity loss, climate change and human interference with the nitrogen cycle), have already been exceeded. They also indicate that humanity may soon be approaching the boundaries for global freshwater use, change in land use, ocean acidification and interference with the global phosphorous cycle.

Currently, the main method of producing food for the earth's growing population is agriculture. Agriculture includes animal farming, and thus provides food from plant and animal sources. Agriculture is closely linked to the overstepping of at least six, maybe seven of the planetary boundaries, i.e. loss of biodiversity, change in land use, global freshwater use, the global nitrogen and phosphorous cycles, chemical pollution, and most likely also climate change.

This is a consequence of modern agriculture being heavily dependent on fossil fuels for working the soil, for transports and for the production and handling of fertilizers and pesticides. Further, the world's soils face exhaustion and depletion, and are at risk from erosion, compaction due to heavy machinery, the accumulation of toxic substances, and the clearing of new land is frequently in conflict with other interests, such as preserving the rain forests and other important biotopes. Approximately 70% of the world-wide water demand is consumed by agriculture, and only about 10% is used as drinking water. Artificial irrigation lowers the ground water table, and the current use of fertilizers and pesticides also risk poisoning the ground water, rivers, lakes and the seas.

The availability of fertilizers, and in particular phosphorus, cannot be taken for granted and there is a risk that the earth's commercial and affordable phosphorous reserves are depleted within a near future. As a consequence, fertilizers are more sparingly used, but nevertheless, large quantities of nutrients reach the marine ecosystems through runoff and cause algal blooms and oxygen depletion. In an attempt to recirculate phosphorus, sewage sludge is spread on farmland. This however requires considerable efforts in handling and transport, and ultimately results in the accumulation of heavy metals and possibly drug residues in the soil.

Large scale animal farming not only causes severe distress for the animals, it requires a constant input of feed that comes from the already heavily taxed soils, and the manure requires closed handling to prevent runoff and consequent pollution. The over-use of antibiotics is another significant risk to human health.

Fishing provides a valuable addition of proteins. However, just like large scale agriculture, large scale industrial fishing has proven detrimental to the marine ecosystems, and many species are on the brink of extinction due to over-fishing. Fish farming has also shown to be plagued by environmental problems. The relatively modern concept of aquaponics, i.e. the combination of growing plants and water living organisms, mainly fish, in a closed system, is very promising. This minimizes pollution and guarantees a more efficient use of nutrients, but still fails to offer the panacea necessary to feed the world's growing population.

Atmospheric carbon dioxide is the main source of available carbon in the carbon cycle, and thus the primary source of carbon for all forms of life on this planet. Carbon dioxide is removed from the atmosphere primarily through photosynthesis and enters the terrestrial and oceanic biospheres in the form of biomass, as part of all living organisms.

Another source of carbon in the atmosphere is methane. Both carbon dioxide and methane absorb and retain heat in the atmosphere and are partially responsible for the greenhouse effect. Methane produces a larger greenhouse effect per volume as compared to carbon dioxide, but it exists in much lower concentrations and is more short-lived than carbon dioxide, making carbon dioxide the more important greenhouse gas of the two.

There is a growing understanding that humanity needs to shift towards a circular economy, and to reduce the environmental impact of our activities. The main focus has so far however been on the production of fuels from renewable sources. Waste products from forestry and agriculture, as well as non-edible plants and algae have been suggested as carbon sources, and many aerobic and anaerobic bioconversion processes have been investigated.

In the review "Fatty acid from the renewable sources: A promising feedstock for the production of biofuels and biobased chemicals" (Biotechnology Advances, 32(2014) 382-389) the authors Hui Liu et al. describe the progress in the biosynthesis of fatty acid and its derivatives from renewable biomass and emphasize the importance of fatty acid serving as the platform chemical and feedstock for a variety of chemicals.

Fang Zhang et al. in the article "Fatty acids production from hydrogen and carbon dioxide by mixed culture in the membrane biofilm reactor" (Water research 47 (2013) 6122-6129) reported that medium chain fatty acids could be produced from $H_2$ and $CO_2$ in a hollow-fiber membrane reactor by mixed microbial culture.

US 20160281115 discloses continuous processes for anaerobic bioconversion of syngas to oxygenated hydrocarbonaceous products, in particular lower alkanols. The use of ultrafiltration makes it possible to recover micronutrients and to reject components adverse to the microorganisms, so that continuous fermentation over long durations can be achieved.

The available prior art appears to have focused on the use of biological processes, and in the majority of cases, on the production of fuels. This does not address the many problems of today, for example the exhaustion and depletion of soils, the high energy requirement, and the environmental impact of agriculture, animal farming and fishing.

SUMMARY

The present inventors here present a truly disruptive solution where electricity is used to produce bioavailable substances from carbon dioxide, the most oxidized form of carbon, and water. One objective is to make available new methods for the synthesis of bioavailable substances and ultimately food, starting directly from energy, oxidized carbon and water. Another objective is to avoid relying on the use of plants and animals for the production of food.

Thus, a first aspect of the present disclosure relates to the use of water and carbon dioxide in a process for the production of edible organic substances, wherein the process comprises the steps of
- electrolysis of water to produce hydrogen and oxygen,
- capture or recovery of carbon dioxide,
- conversion of said carbon dioxide to carbon monoxide,
- subjecting said hydrogen and carbon monoxide to a Fischer-Tropsch synthesis to produce a mixture of olefins,
- optionally increasing the proportion of ethylene by coupling of methane to form ethylene, and/or convert higher olefins to form ethylene,
- isolating ethylene,
- synthesizing alpha-olefins or fatty acid alcohols from said ethylene, and
- oxidizing said alpha-olefins or fatty acid alcohols to free fatty acids, wherein the net energy input is in the form of electricity.

A second aspect relates to the use of water and carbon dioxide in a process for the production of edible organic substances, wherein said process comprises the steps of
- electrolysis of water to produce hydrogen and oxygen,
- capture or recovery of carbon dioxide,
- subjecting said hydrogen and carbon dioxide to catalytic synthesis to produce methanol,
- converting said methanol to a mixture of olefins,
- optionally converting propylene and higher olefins to produce ethylene,
- isolating ethylene,
- synthesizing alpha-olefins or fatty acid alcohols from said ethylene, and
- oxidizing said alpha-olefins or fatty acid alcohols to free fatty acids, wherein the net energy input is in the form of electricity.

According to an embodiment of said first or second aspect, the process further comprises a step of adding glycerol and esterifying said free fatty acids to triglycerides.

According to another embodiment of said first or second aspect, freely combinable with the above, the oxygen produced in the electrolysis step is led into a combustion unit for the combustion of organic matter, and carbon dioxide is captured/recovered from flue gases from said combustion.

A third aspect relates to a method for the production of edible organic substances, said method comprising the steps
- electrolysis of water to produce hydrogen and oxygen,
- capture or recovery of carbon dioxide,
- conversion of said carbon dioxide to carbon monoxide,
- subjecting said hydrogen and carbon monoxide to a Fischer-Tropsch synthesis to produce a mixture of olefins,
- optionally increasing the proportion of ethylene by coupling of methane to form ethylene, and/or converting, for example cracking higher olefins to form ethylene,
- isolating ethylene,
- synthesizing alpha-olefins or fatty acid alcohols from said ethylene, and
- oxidizing said alpha-olefins or fatty acid alcohols to free fatty acids.

According to an embodiment of said third aspect, said electrolysis step is a high-temperature electrolysis step, and waste heat from the Fischer-Tropsch synthesis is used to generate steam for said high-temperature electrolysis step.

A fourth aspect relates to a method for the production of edible organic substances, said method comprising the steps
- electrolysis of water to produce hydrogen and oxygen,
- capture or recovery of carbon dioxide,
- subjecting said hydrogen and carbon dioxide to catalytic synthesis to produce methanol,
- converting said methanol to a mixture of olefins,
- optionally converting propylene and higher olefins to produce ethylene,
- isolating ethylene,
- synthesizing alpha-olefins or fatty acid alcohols from said ethylene, and
- oxidizing said alpha-olefins or fatty acid alcohols to free fatty acids.

According to an embodiment of said fourth aspect, said electrolysis step is a high-temperature electrolysis step, and waste heat from the exothermic methanol synthesis is used to generate steam for said high-temperature electrolysis step.

According to an embodiment of said third or fourth aspect, freely combinable with the other aspects and embodiments, the method further includes a step of adding glycerol and esterifying said free fatty acids to triglycerides.

According to another embodiment of said third or fourth aspect, freely combinable with the other aspects and embodiments, the oxygen produced in the electrolysis step is led into a combustion unit for the combustion of organic matter, and carbon dioxide is captured/recovered from flue gases from said combustion.

According to yet another embodiment of said third or fourth aspect, freely combinable with the other aspects and embodiments, the net energy input is in the form of electricity.

According to a further embodiment of said third or fourth aspect, freely combinable with the other aspects and embodiments, the free fatty acids as such, or after esterification to triglycerides, are formulated (blended, processed etc) into food products for human consumption.

According to another embodiment of said third or fourth aspect, freely combinable with the other aspects and embodiments, the free fatty acids as such, or after esterification to triglycerides, are formulated (blended, processed etc) into feed products for animal consumption.

According to a further embodiment of said third or fourth aspect, freely combinable with the other aspects and embodiments, the free fatty acids as such, or after esterification to triglycerides, are used as feed for cell cultures, said cells chosen from yeast cells, bacterial cells, fungal cells, plant cells or non-human animal cells.

According to yet another embodiment of said third or fourth aspect, freely combinable with the other aspects and embodiments, the triglycerides or lipids are used as feed for insects, and said insects are harvested for the production of food.

According to yet another embodiment of said third or fourth aspect, freely combinable with the other aspects and embodiments, the triglycerides or lipids are used as feed for animals, reducing the need for plant-based feed when raising animals.

A fifth aspect relates to food or feed products produced by a method according to any one of the above aspects and embodiments.

SHORT DESCRIPTION OF THE FIGURES

The invention is now described, by way of example, with reference to the accompanying drawings, in which.

DETAILED DESCRIPTION

Figure 1:
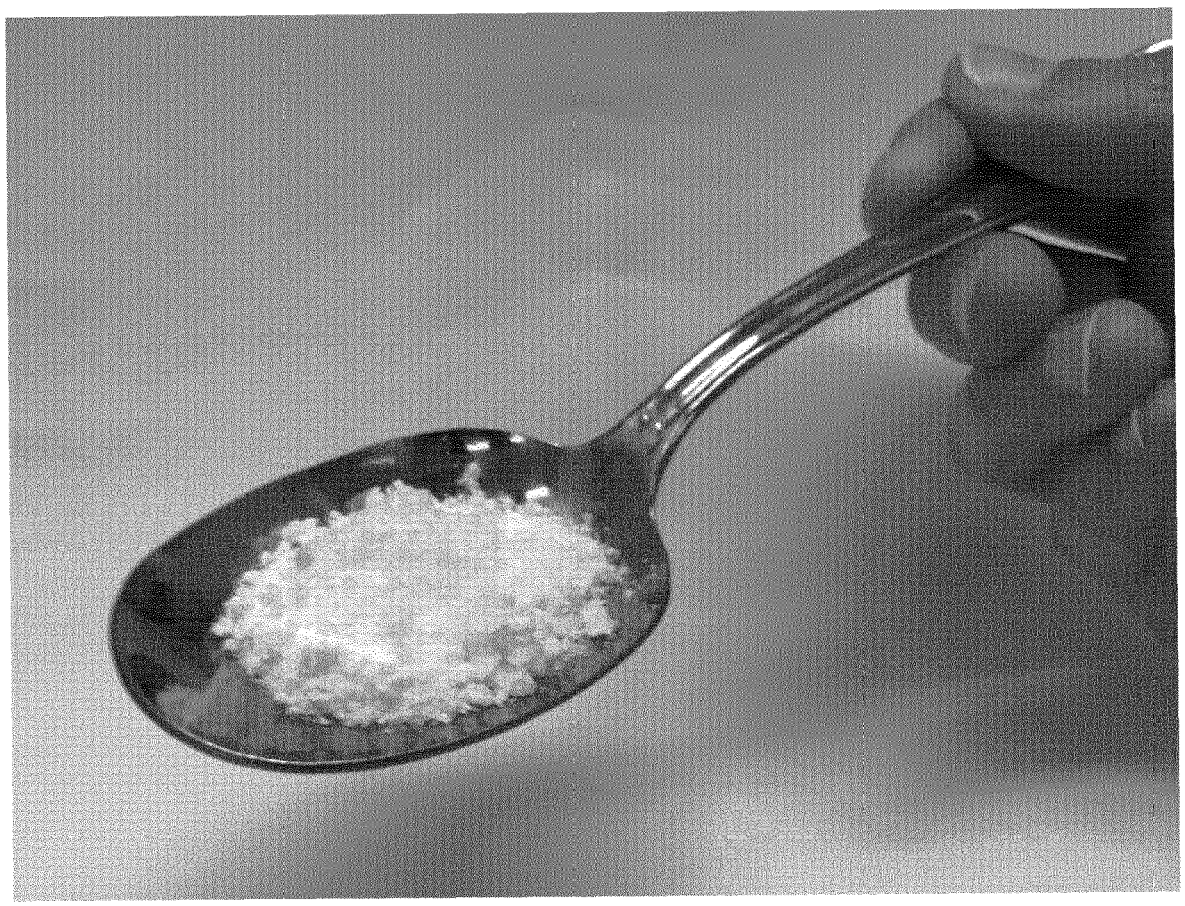
FIG. 1 is a photograph showing a portion of the synthetic fatty acids (a C16/C18 mixture) obtained as a white solid in Example 3.
Figure 2:
FIG. 2 is a photograph showing a portion of the glyceryl tripalmitate obtained in Example 4.

Before the present invention is described, it is to be understood that the terminology employed herein is used for the purpose of describing particular embodiments only and is not intended to be limiting, since the scope of the present invention will be limited only by the appended claims and equivalents thereof.

It must be noted that, as used in this specification and the appended claims, the singular forms "a," "an," and "the" include plural referents unless the context clearly dictates otherwise.

The terms "food" and "feed" are used to define substances and formulations that can be safely ingested by humans (food) and animals (feed), including snacks, beverages, solid and liquid food and feed formulations.

The term "edible" is used to describe that a substance is generally recognized, among qualified experts, as having been adequately shown to be safe under the conditions of its intended use, i.e. eaten as food or feed, or ingested as a component of food or feed. According to the online version of the Cambridge dictionary (https://dictionary.cambridge.org/) the adjective "edible" refers to something suitable or safe for eating. It is recognized that the distinction between "edible" and "poisonous" is relative, as the dosage is decisive. Common ingredients in food, such as table salt (sodium chloride) or sugar (glucose) are considered edible, although an overdose of both can be lethal. For sodium chloride, the LD50 is 3 g/kg bodyweight and for sucrose, 29.7 g/kg. Thus, for an adult human, the intake of about 200 g table salt or about 2 kg sugar could be lethal, nevertheless both substances are considered "edible" under the conditions of their intended use, as components in food. Similarly, although an excessive intake of dietary lipids can be unhealthy, fatty acids and triglycerides are considered edible or safe when consumed in a normal diet, as they are degraded by salivary, intestinal and pancreatic lipases.

The terms "capture" and "recovery" are intended to encompass existing and future techniques for separating and concentrating carbon dioxide from a solid, liquid or gaseous medium, for example—but not limited to—pre-combustion carbon capture, post-combustion carbon, oxy-fuel combustion carbon capture, and direct air capture. Available technologies today include unit operations such as filtering, absorption, catalytic conversion, cooling and compression. These technologies are already available to persons skilled in the art, in addition to new technologies under development.

The term "converting" refers in general to the process of changing the form or character of a compound, such as changing a hydrocarbon from a saturated into an unsaturated form, or vice versa, adding or removing a carbon etc. There are many methods for converting hydrocarbons, see e.g. The Chemistry of Catalytic Hydrocarbon Conversions, Herman Pines, Academic Press, 1981.

The term "cracking" refers to methods where longer hydrocarbons are broken down into shorter, often unsaturated, hydrocarbons. There are several established methods of cracking, such as thermal cracking and catalytic cracking. Two of the most intensive and commonly used catalytic cracking processes in petroleum refining are fluid catalytic cracking and hydrocracking. Suitable cracking processes and their parameters can be chosen by a person skilled in the art, relying on public information, such as the "Handbook of Petroleum Refining Processes", Robert A. Meyers (Ed.), 4th Edition, McGraw-Hill Education; March 2016.

The present inventors advocate the use of synthetically produced edible free fatty acids—either directly or optionally after esterification to triglycerides—as food for humans, as components in human food or as components in animal feed, or as feed for cell cultures, wherein said free fatty acids are produced in a process where the net energy input is in the form of electricity, and the starting materials are only carbon dioxide and water. Carbon dioxide is available in the atmosphere, where increasing levels are contributing to the greenhouse effect and global warming. Water is freely available, in particular as the water will be subjected to electrolysis, recovering the hydrogen which is formed. It will thus be possible to use polluted water, and as an advantageous side effect, the electrolysis will contribute to breaking down chemical and microbial pollutants, thus purifying the water.

Thus, a first aspect of the present disclosure relates to the use of water and carbon dioxide in a process for the production of edible organic substances, wherein the process comprises the steps of
  electrolysis of water to produce hydrogen and oxygen,
  capture or recovery of carbon dioxide,
  conversion of said carbon dioxide to carbon monoxide,
  subjecting said hydrogen and carbon monoxide to a Fischer-Tropsch synthesis to produce a mixture of olefins,
  optionally increasing the proportion of ethylene by coupling of methane to form ethylene, and/or converting, for example cracking higher olefins to form ethylene,
  isolating ethylene,
  synthesizing alpha-olefins or fatty acid alcohols from said ethylene, and
  oxidizing said alpha-olefins or fatty acid alcohols to free fatty acids,
wherein the net energy input is in the form of electricity.

A second aspect relates to the use of water and carbon dioxide in a process for the production of edible organic substances, wherein said process comprises the steps of
  electrolysis of water to produce hydrogen and oxygen,
  capture or recovery of carbon dioxide, subjecting said hydrogen and carbon dioxide to catalytic synthesis to produce methanol, converting said methanol to a mixture of olefins, optionally converting propylene and higher olefins to produce ethylene isolating ethylene, synthesizing alpha-olefins or fatty acid alcohols from said ethylene, and oxidizing said alpha-olefins or fatty acid alcohols to free fatty acids, wherein the net energy input is in the form of electricity.

The source of the energy is preferably a renewable source, and more preferably a low-emission source and most preferably a zero-emission source, such as photovoltaics, wind power or hydroelectric power including wave and tidal power.

As an alternative to electrolysis, the separation of water into hydrogen and oxygen can be achieved by other methods, such as but not limited to proton exchange membrane (PEM) electrolysis, and alkaline water electrolysis.

According to an embodiment of said first or second aspect, the process further comprises a step of adding glycerol and esterifying said free fatty acids to triglycerides.

According to another embodiment of said first or second aspect, freely combinable with the above, the oxygen produced in the electrolysis step is led into a combustion unit for the combustion of organic matter, and carbon dioxide is captured/recovered from flue gases from said combustion.

This embodiment is particularly advantageous when a plant for the production of edible organic substances operating according to the methods disclosed herein is located in the vicinity of a power station relying on the combustion of organic fuel (for example biofuels, coal, oil, natural gas, recycled plastics, municipal or industrial waste, or by-products or waste from agriculture, forestry or food industry). The power station generates electricity which is used for the electrolysis of water (which can be waste water, aiding in the purification of said waste water) and the oxygen formed as a by-product of said electrolysis is fed into the combustion unit of said power station.

A similar set-up preferably arranged at other point-sources of carbon dioxide, such as cement factories, iron and steel industry, and petrochemical refineries to name a few examples. Cement manufacturing is a significant source of carbon dioxide emissions, both directly when calcium carbonate is heated, producing lime and carbon dioxide, and indirectly, through the use of energy if the production of said energy involves emissions of carbon dioxide. It is estimated that the cement industry accounts for about 10% of the global man-made CO2 emissions.

A third aspect relates to a method for the production of edible organic substances, said method comprising the steps electrolysis of water to produce hydrogen and oxygen, capture or recovery of carbon dioxide, conversion of said carbon dioxide to carbon monoxide, subjecting said hydrogen and carbon monoxide to a Fischer-Tropsch synthesis to produce a mixture of olefins, optionally increasing the proportion of ethylene by coupling of methane to form ethylene, and/or converting, for example cracking higher olefins to form ethylene, isolating ethylene, synthesizing alpha-olefins or fatty acid alcohols from said ethylene, and oxidizing said alpha-olefins or fatty acid alcohols to free fatty acids.

According to an embodiment of said third aspect, said electrolysis step is a high-temperature electrolysis step, and waste heat from the Fischer-Tropsch synthesis is used to generate steam for said high-temperature electrolysis step.

A fourth aspect relates to a method for the production of edible organic substances, said method comprising the steps electrolysis of water to produce hydrogen and oxygen, capture or recovery of carbon dioxide, subjecting said hydrogen and carbon dioxide to catalytic synthesis to produce methanol, converting said methanol to a mixture of olefins, optionally converting propylene and higher olefins to produce ethylene isolating ethylene, synthesizing alpha-olefins or fatty acid alcohols from said ethylene, oxidizing said alpha-olefins or fatty acid alcohols to free fatty acids.

According to an embodiment of said fourth aspect, said electrolysis step is a high-temperature electrolysis step, and waste heat from the exothermic methanol synthesis is used to generate steam for said high-temperature electrolysis step.

According to an embodiment of said third or fourth aspect, freely combinable with the other aspects and embodiments, the method further includes a step of adding glycerol and esterifying said free fatty acids to triglycerides.

According to another embodiment of said third or fourth aspect, freely combinable with the other aspects and embodiments, the oxygen produced in the electrolysis step is led into a combustion unit for the combustion of organic matter, and carbon dioxide is captured/recovered from flue gases from said combustion.

According to yet another embodiment of said third or fourth aspect, freely combinable with the other aspects and embodiments, the net energy input is in the form of electricity.

According to a further embodiment of said third or fourth aspect, freely combinable with the other aspects and embodiments, the free fatty acids as such, or after esterification to triglycerides, are formulated (blended, processed etc) into food products for human consumption.

According to another embodiment of said third or fourth aspect, freely combinable with the other aspects and embodiments, the free fatty acids as such, or after esterification to triglycerides, are formulated (blended, processed etc) into feed products for animal consumption.

According to a further embodiment of said third or fourth aspect, freely combinable with the other aspects and embodiments, the free fatty acids as such, or after esterification to triglycerides, are used as feed for cell cultures, said cells chosen from yeast cells, bacterial cells, fungal cells, plant cells or non-human animal cells.

According to yet another embodiment of said third or fourth aspect, freely combinable with the other aspects and embodiments, the triglycerides or lipids are used as feed for insects, and said insects are harvested for the production of food.

According to yet another embodiment of said third or fourth aspect, freely combinable with the other aspects and embodiments, the triglycerides or lipids are used as feed for animals, reducing the need for plant-based feed when raising animals.

A fifth aspect relates to food or feed products produced by a method according to any one of the above aspects and embodiments.

Figure 3:
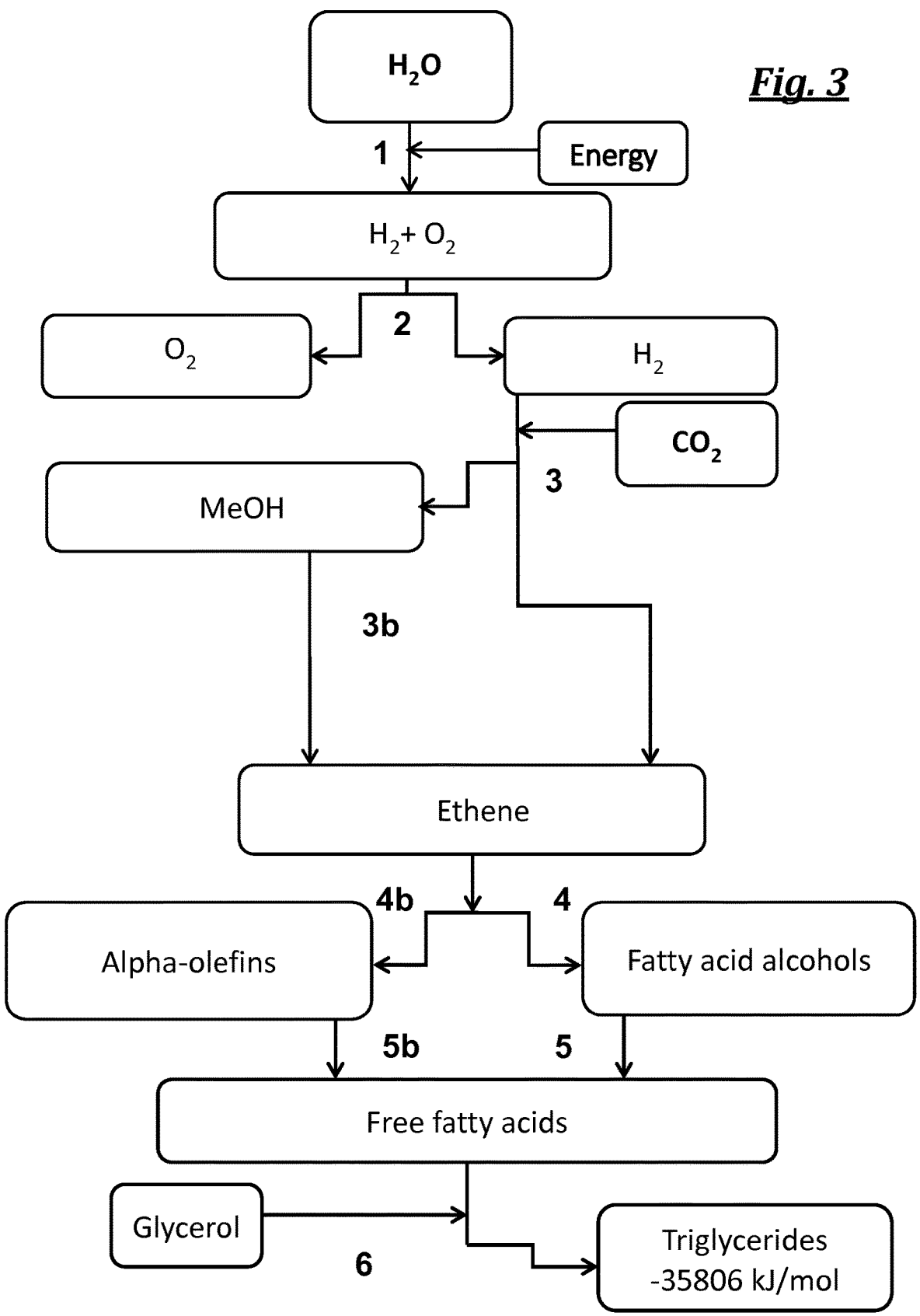
FIG. 3 shows a synthesis scheme illustrating the concept of the invention and showing alternative synthesis pathways and indicating the energy content as heat of combustion (kJ/mol) as obtained from the NIST Chemistry WebBook, SRD 69, published by the National Institute of Standards and Technology, U.S. Department of Commerce.

As shown in the synthesis scheme presented in FIG. 3, the starting point is water ($H_2O$) which is subjected to electrolysis (1), preferably high-temperature electrolysis, which decomposes the water into oxygen ($O_2$) and hydrogen ($H_2$) gas. Hydrogen gas is separated (2) and used in the claimed process. The resulting oxygen can be released into the ambient, or concentrated and collected for use in chemical industries, in the production of iron and steel, or for other uses.

The hydrogen gas is then used for producing syngas, for example using a process referred to as the reverse water-gas shift reaction (RWGS) where carbon dioxide and hydrogen are reacted in the presence of a catalyst to form syngas. Such processes are known, for example through EP 2175986 A2 which discloses a reverse water gas shift reaction on a catalyst substantially consisting of chromium on an alumina support.

The hydrogen can also be reacted with carbon dioxide, forming syngas. In the synthesis scheme in FIG. 3, this route is indicated as (3) and then also includes Fischer-Tropsch chemistry for converting the syngas into olefins. An example of a process for producing ethylene and propylene from syngas using a catalyst composition is disclosed in US 2014128486 A1. Said the process comprises the steps of a) contacting syngas with a first catalyst composition to obtain a first product stream comprising ethylene, propylene and aliphatic hydrocarbons having 4 or more carbon atoms, b) splitting the first product stream into a second product stream comprising at least 90% of said aliphatic hydrocarbons having four or more carbon atoms and a third product stream comprising ethylene and propylene, c) separating ethylene and propylene in the third product stream so as to form a first ethylene stream and a first propylene stream and d) converting the second product stream into a fourth product stream comprising ethylene and/or propylene.

In an alternative pathway, the syngas is used to produce methanol, for example using the so-called CRI process, named after Carbon Recycling International, an Icelandic company, and disclosed for example in U.S. Pat. No. 8,198, 338. The resulting methanol can then be converted into olefins using the MTO (methanol-to-olefins) process, disclosed for example in U.S. Pat. No. 6,166,282. This is indicated in FIG. 3 as the pathway 3*b*.

The MTO process catalytically converts oxygenates, such as methanol, to light olefins. Typically, a fluidized bed using SAPO (silicoaluminophosphate) catalysts is preferred and the composition of the light olefins is preferably directed towards high ethylene yield. Such a direction can be achieved by a combination of this technology with aftertreatment steps such as olefin cracking (UOP/Total OCP) or conversion of olefins to form ethylene, and can result in more efficient feedstock efficiency.

An example of an MTO plant among many is the Lianyungang plant operated by Jiangsu Sailboat Petrochemical Co., Ltd, Jiangsu, China, using the OLEFLEX™ technology supplied by Honeywell UOP, Des Plaines, USA.

Ethylene is then converted to fatty acid alcohols using either the Shell Higher Olefin Process (SHOP) or the Ziegler-ALFOL® process, using suitable catalysts, for example organoaluminium catalysts. This pathway is indicated as 4 in FIG. 3. The reaction produces linear primary alcohols with an even numbered carbon chain. The primary alcohols can be modified further to fatty acid alcohols, which are then oxidized (5) to produce free fatty acids. Both the resulting alpha olefins and the alcohols are then oxidized to yield aliphatic carboxylic acids (free fatty acids, FFA) with an even number of carbon atoms.

In the alternative, using SHOP, the olefins are converted to fatty aldehydes and then to fatty alcohols, which are then further oxidized to free fatty acids. Adding glycerol to the fatty acids, any triglyceride of interest can be synthesized using known esterification reactions (6).

Esterification of fatty acids with glycerol to form triglycerides (fat) can also be performed with limiting stoichiometry for the fatty acid, or by selective enzymes, resulting in mono- or di-glycerides. These substances are commonly used in combination as emulsifiers in foods, helping to prevent mixtures of oils and water from separating. They are often used in bakery products, beverages, ice cream, shortening and margarine. Production of mono- and di-glycerides via the disclosed pathways is therefore a good complement to the primary fat production, enabling formulation of food and feed products.

The esterification is preferably performed by Fisher-esterification (see for example "Name Reactions and Reagents in Organic Synthesis" by Bradford P. Mundy et al., $2^{nd}$ Ed., Wiley Interscience, 2005, ISBN 0471228540) but can also be performed using other known methods such as transesterification (U.S. Pat. No. 7,067,684), enzyme catalysis (WO 90/12858) or by other organic reactions such as fatty acid chloride coupling with glycerol (Fatty Acids and Glycerides (Handbook of Lipid Research), A. Kuksis (Ed.), Springer, ISBN 978-1-4684-2567-3).

One advantage is that the inventive concept relies on known and proven methods, already in large-scale use. Another advantage is that the method is energy efficient, and low cost as the amount labour is significantly reduced. The method also uses the resources (for example water, carbon, hydrogen, nitrogen, oxygen, and phosphorus) very efficiently, as the production takes place in closed systems, thus avoiding any runoff of nutrients.

Compared to biotechnical approaches to the production of food, such as cell-culture based processes, the inventive process minimizes the use of water, nitrogen and phosphorous, three components where the planetary boundaries are at risk.

An added advantage is that the methods allow the simultaneous and/or parallel synthetic production of several components of food, not only the fat which normally provides half of the body's energy needs, but also important additives, for example emulsifiers such as mono- or di-glycerides which influence texture, consistency and smoothness of food products, and flavouring agents, such as aldehydes, which contribute with specific aromas associated with different foodstuffs.

The methods are also more robust than traditional farming, as they are insensitive to periods of draught, storms, insects, pests etc. In polluted areas, the methods make it possible to produce food without the risk of including for example heavy metals or pesticide residues in the end product. The production facilities can also be located in areas otherwise unsuitable for traditional food production, such as deserts, mountains, Arctic/Antarctic areas.

From an environmental point of view, the methods are very advantageous, as it minimizes land use. Thus, remaining untouched biotopes can be saved. Additionally, current farmland could be restored, and biodiversity rebuilt. When the energy comes from renewable sources, and the starting material $CO_2$ is captured from the atmosphere or recovered from industrial processes, the only greenhouse gas emissions come from transportation and distribution, unless these operations can be powered using energy from renewable sources, for example electrical vehicles or vehicles running on low-emission biofuels.

From an ethical point of view, the methods have the advantage that no animals or plants are harmed in any way.

It will also be possible to make the production of food available to all countries, regardless of factors such as climate, availability of fertile soils, water etc. It is also ethically advantageous that a growing population could potentially be fed without causing irreparable harm to the biosphere.

Based on information disclosed in the report "Power-to-Liquids: Potentials and Perspectives for the Future Supply of Renewable Aviation Fuel" by Patrick Schmidt and Arne Roth, published by the German Environment Agency in September 2016, it is estimated that the energy conservation achieved by the claimed method would be about 50% for intermediates, and an estimated 25% for final food products, the last figure however depending on the process integration, i.e. the efficiency in handling and processing of materials between different steps from start to final product.

The production of 100 kg food using the claimed method is estimated to result in the uptake of 300 kg $CO_2$, given that one mole of $CO_2$ loses ⅔ of its molecular weight when reduced with $H_2$ to yield —$CH_2$— based fatty acids and triglycerides. The cost of the process is highly dependent on the cost for generating the energy, but assuming that the investment in installations for renewable energy such as photovoltaics, wind power, hydrothermal power, geothermal power, hydropower, nuclear and wave power is carried by society as a whole, the cost for producing 100 kg free fatty acids for use as food or feed is estimated to about 100-1000 EUR.

EXAMPLES

Example 1. Production of Free Fatty Acids Using the Fischer-Tropsch Synthesis An integrated production line is established in a refinery-like setup. The setup is a combination of existing processes based on electrolysis of water, production of olefins via Fischer-Tropsch processes followed by conversion to ethylene and consecutive production of even-carbon chain saturated fatty acids via alpha-olefins or via fatty acid alcohol synthesis. The process steps are integrated by a combination of industrial pathways, for example, hydrogen production, fuel production, lubrication oil production and detergent production. These pathways are integrated to achieve optimal efficiency and scale-up gains.

The production facility is preferably located at a large $CO_2$ emission source such as a combustion power plant, a power plant, cement mill, paper mill, fermentation plant or biogas production unit. Also, water abundancy and good infrastructure in general is preferable, and in fact, the facility could be situated similarly to a common refinery. The produced fatty acids are both supplied directly to the animal feed industry as well as converted to triglycerides for supply as feed and human food.

$CO_2$ is harvested using appropriate carbon capture technology. If the $CO_2$ emission source is a fermentation and biogas plant, a less complex technology can be used due to the high $CO_2$ concentration in those streams. Gas streams with a lower $CO_2$ content need to be upgraded, for example using scrubbers, preferably using MEA (monoethanolamine) or other amines. The concentrated $CO_2$ stream is then reformed with electrolytically generated $H_2$ (from water) to produce synthesis gas.

Fischer-Tropsch technology is then used for production of ethylene and propylene. The ethylene is separated and used as an even-carbon building block to synthesize aliphatic alcohols or aliphatic alpha olefins. Surplus propylene can be used for other synthesis or converted to form ethylene. Industrial processes based on the work of Dr. Karl Ziegler and improvements thereof are preferred (for example the Ziegler-ALFOL® process developed by Conoco, and the EPAL® process developed by Ethyl Corporation).

Both the resulting alpha-olefins and the alcohols are then oxidized to yield aliphatic carboxylic acids (free fatty acids, FFA) with an even number of carbon atoms. A range of molecular weights are produced, aiming at the ones found in nature, that is the range $C_{12}$-$C_{22}$. These carboxylic acids are then purified by distillation and form one of the end products and can be used as an energy source for humans and animals. Further, the carboxylic acids are reacted, using Fischer esterification with glycerol to form triglycerides (fat). The second end product is thus fat, that can be used for food and feed. Triglycerides are the preferred energy carrier in this example since they are easily formulated with other ingredients in food and feed, have a neutral or even pleasant taste and are the most common of the two, used throughout the global food industry.

Example 2. Production of Free Fatty Acids Using the MTO Synthesis

Alternatively, a concentrated $CO_2$ stream obtained from a point source, or obtained by concentrating $CO_2$ from any other source, is then reacted with electrolytically generated $H_2$ (from water) to produce methanol, using one of the methanol-synthesis procedures available, for example the method described by Akzo Nobel or the commercially available technology from CRI. The methanol production is the first key step for chemically reducing the $CO_2$ and thereby incorporate electrical energy into the molecule. The physical properties of methanol as an intermediate are also favourable since it's a liquid and can easily be stored and transported. Methanol is then reacted using the MTO (methanol-to-olefins) process to produce ethylene and propylene. The ethylene is separated and used as an even-carbon building block to synthesize aliphatic alcohols or aliphatic alpha olefins.

Industrial processes based on the work of Dr. Karl Ziegler and improvements thereof are preferred (for example the Ziegler-ALFOL® process developed by Conoco, and the EPAL® process developed by Ethyl Corporation).

Both the resulting alpha olefins and the alcohols are then oxidized to yield aliphatic carboxylic acids (free fatty acids, FFA) with an even number of carbon atoms. A range of molecular weights are produced, aiming at the ones found in nature, that is the range $C_{12}$-$C_{22}$. These carboxylic acids are then purified by distillation and form one of the end products and can be used as an energy source for humans and animals. Further, the carboxylic acids are reacted, using Fischer esterification with glycerol to form triglycerides (fat). As in Example 1, this example outlines the production of free fatty acids and fat starting from $CO_2$, water, and energy.

Example 3. Lab-Scale Synthesis of C16/C18 Fatty Acids

Ethylene is used to produce aliphatic alcohols with an even number of carbons. These are then oxidized in one of two ways to produce free fatty acids, the raw-material for feed and food. It is known that there are several methods for oxidizing alcohols, for example using ozone, oxygen, permanganate, nitric acid and enzymes. These regents in combination with a variety of catalysts are central building blocks in the field of green chemical oxidation reviewed by Sheldon (Roger A. Sheldon, Green Oxidation in Water, in Handbook of Green Chemistry, 2010, © 2010 Wiley-VCH Verlag GmbH & Co. KGaA.). Two examples of relevant oxidations to produce free fatty acids are given below:

3.1 Oxidation with $O_2$ 1.52 g (6.03 mmol) cetearyl alcohol (NAFOL1618, Sasol Performance Chemicals) was dissolved in 25 mL 1,2-dichloroethane (DCE) in a 100 mL flask by stirring for 20 min followed by addition of Fe(NO3)3.9H2O (0.24 g, 0.60 mmol), KCl (45 mg, 0.60 mmol) and (2,2,6,6-Tetramethylpiperidin-1-yl)oxyl (TEMPO) (94 mg, 0.60 mmol). The flask was then connected to vacuum followed by the addition of $O_2$ from a 5 L balloon. The vacuum/oxygen procedure was repeated twice. After 22 h of stirring at room temperature in an oxygen atmosphere, the reaction mixture was filtrated through a short silica gel column eluted with dichloromethane (DCM) (100 mL) and ethyl acetate (2×75 mL). After evaporation and vacuum over night at 40° C. the title compounds (C16/C18 mixture) were obtained as a white solid (1.546 g, 96%) NMR (500 MHz, CDCl3) δ 2.36 (t, J=Hz, 2H, CH2), 1.63-1.68 (m, 2H, CH2), 1.25-1.38 (m, 24/28H, 12/14×CH2), 0.89 (t, J=Hz, 3H, CH3). See FIG. 1.

Cetearyl alcohol (e.g. NAFOL® 1618) is a mixture of fatty alcohols, consisting predominantly of cetyl (16 C) and stearyl alcohols (18 C), and is conveniently produced using the Ziegler process. Notably, the supplier (Sasol) presents this and related products as "Ziegler alcohols".

Additionally, the method disclosed above can be used with different solvents and oxidized with air instead of $O_2$.

3.2 Oxidation with $HNO_3$

To a stirred and heated (55° C.) heptane (0.3 ml) solution of the appropriate fatty acid alcohol (50 mg, approx. 0.2 mmol of a hexadecanol/octadecanol mixture), an excess of the oxidizing nitric acid $HNO_3$ (99%, 0.25 ml, 4 mmol) was added slowly. The two-phase system was reacted for 18 hours under atmospheric pressure. The formed $NO_2$ gas was removed from the reaction vessel during the reaction. The reaction mixture was washed with brine (10 ml) and the formed fatty acids was collected by harvesting the heptane phase. A white solid was collected after evaporation of the heptane and characterized with GC/MS, revealing the main reaction products as hexadecanoic acid and octadecanoic acid. The carboxylic acids were formed with 85% conversion.

Example 4. Lab Scale Synthesis of Glyceryl Tripalmitate

Glyceryl tripalmitate, also called palmitin, is an ester of glycerol and palmitic acid. It is found abundantly in animals and vegetables, for example in palm oil, which explains the name (palmitin). It is also a component of butter and olive oil, where it is found in admixture with other fats. Here, glyceryl tripalmitate is chosen as an example of a fat that can be synthesized from free fatty acids produced as disclosed herein.

Palmitic acid (5:20 g, 20.27 mmol), pTsOH (61 mg, 338 μmol) and glycerol (500 μL, 6:76 mmol) were successively added to a 50 mL round bottom flask. The reaction was placed under gentle vacuum and a low flow of nitrogen was bubbled into the reaction mixture. The reaction was heated to 115° C. until total disappearance of the palmitic acid monitored by GC-MS (15 hours). At this stage an NMR sample was taken to ensure that all the material had converted to the tri ester.

The reaction mixture was the cooled to ambient temperature and 50 mL of toluene was added to the solid that was filtered off. The solid was then recrystallized from toluene (20-30 mL) and finally recrystallized from acetone (20 mL). The resulting white solid was placed in an oven vacuum at 40° C. overnight to give 3.3 g of the desired tri ester product (61% yield). NMR (1H 500 MHz, CDCl3) δ 5.27 (m, 1H), 4.30 (dd, J=11.9, 4.3 Hz, 1H), 4.15 (dd, J=11.9, 6.0 Hz, 1H), 2.32 (m, 6H), 1.60 (m, 6H), 1.30 (m, 72H), 0.89 (app t, J=6.85 Hz, 9H).

Example 5. Food Production

Substances produced via the described processes are administered directly, or as formulations/mixtures, to humans. Free fatty acids play an important role in the aroma and flavour of many dairy products, such as milk, butter and cheese. Synthetic free fatty acids can thus be used to produced non-dairy substitutes for such products. The synthetic free fatty acids produced as in the present disclosure can also be used to produce nutritional supplements and to fortify existing foods, such as plant oils, or to produce synthetic non-dairy and non-plant based oils so as to reduce the impact of agriculture, depletion of soil, leakage of nutrients, the need new arable land, and thereby to avoid the destruction of tropical rainforests for the production of e.g. palm oil. Persons skilled in the art of refining and formulating plant oil-based products, such as cooking oils, are also capable of refining and formulating synthetic substitutes based on the free fatty acids disclosed herein.

Fats can be processed into stable emulsions by vigorously mixing fat, water and one or more emulsifiers, and optionally adding flavouring, food dyes, vitamins and other additives well-known to persons skilled in the art of food processing. Examples of products obtainable from the synthetic fats disclosed herein include but are not limited to non-dairy milk and cream substitutes, non-dairy cheese, spreads, and ice-cream. The synthetic fats can also be incorporated into cereal or legume-based products, such as snacks, ready meals, baked goods etc.

As the substances are identical to nutritional substances found in conventional food, they will contribute to the human metabolism. For humans, maintaining the body temperature is a main energy sink and the substances produced according to the concept, methods and processes disclosed herein can be used as a fundamental energy supply for this purpose and thereby complement a diversified diet. A unique feature of this concept is that the energy gained by the human body this way is indirectly produced by electricity and carried via the produced substances, such as fatty acids or triglycerides.

Example 6. Feed Production

Alternatively, substances produced via the described processes, for example triglycerides in the $C_{12}$-$C_{22}$ range or their fatty acid analogues, are administered to animals directly, or as feed formulations or mixtures, or added to or as a supplement to feed and fodder, or as a nutritional supplement to grazing animals, for example to cattle, pigs, poultry, or even to insects. The energy gained by the animals is a part of their metabolism and will contribute to the growth of their body. The animals are thereafter harvested as in conventional farming, processed into various food products and supplied to humans as food (beef, minced meat, chicken nuggets etc).

A person skilled in the art of feed formulation is well familiar with the unit operations of mixing, blending, milling, pelleting and packaging of animal feeds, regardless if intended for livestock, poultry or aquatic animals. As a first step, the free fatty acids and fats produced according to the present disclosure can be used to supplement existing feeds. The goal is however to eventually replace plant based free fatty acids and fats with their synthetic counterparts, and to minimize and eventually eliminate to use of farm land for the production of feed.

Without further elaboration, it is believed that a person skilled in the art can, using the present description, including the examples, utilize the present invention to its fullest extent. Also, although the invention has been described herein with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

Thus, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A method for the production of edible organic substances, said method comprising the steps
   electrolysis of water to produce hydrogen and oxygen,
   capture or recovery of carbon dioxide,
   conversion of said carbon dioxide to carbon monoxide,
   subjecting said hydrogen and carbon monoxide to a Fischer-Tropsch synthesis to produce a mixture of olefins,
   optionally increasing the proportion of ethylene by coupling of methane to form ethylene, and/or converting higher olefins to form ethylene,
   isolating ethylene,
   synthesizing alpha-olefins or fatty acid alcohols from said ethylene, and
   oxidizing said alpha-olefins or fatty acid alcohols to free fatty acids with an even number of carbon atoms,
   wherein the net energy input is in the form of electricity.

2. The method according to claim 1, wherein said electrolysis step is a high-temperature electrolysis step, and wherein waste heat from the Fischer-Tropsch synthesis is used to generate steam for said high-temperature electrolysis step.

3. A method for the production of edible organic substances, said method comprising the steps
   electrolysis of water to produce hydrogen and oxygen,
   capture or recovery of carbon dioxide,
   subjecting said hydrogen and carbon dioxide to catalytic synthesis to produce methanol,
   converting said methanol to a mixture of olefins,
   optionally converting higher olefins to produce ethylene,
   isolating ethylene,
   synthesizing alpha-olefins or fatty acid alcohols from said ethylene,
   oxidizing said alpha-olefins or fatty acid alcohols to free fatty acids with an even number of carbon atoms,
   wherein the net energy input is in the form of electricity.

4. The method according to claim 3, wherein said electrolysis step is a high-temperature electrolysis step, and wherein waste heat from exothermic methanol synthesis is used to generate steam for said high-temperature electrolysis step.

5. The method according to claim 1, further including a step of adding glycerol and esterifying said free fatty acids to triglycerides.

6. The method according to claim 1, wherein oxygen produced in the electrolysis step is led into a combustion unit for the combustion of organic matter, and carbon dioxide is captured/recovered from flue gases from said combustion.

7. The method according to claim 1, wherein the free fatty acids as such, or after esterification to triglycerides, are formulated into food for human consumption.

8. The method according to claim 1, wherein the free fatty acids as such, or after esterification to triglycerides, are formulated into feed for animal consumption.

9. The method according to claim 1, wherein the free fatty acids as such, or after esterification to triglycerides, are added to culture media for the growing of cells, said cells chosen from yeast cells, bacterial cells, fungal cells, plant cells or non-human animal cells.

10. The method according to claim 5, wherein the triglycerides are used as feed for insects, and said insects are harvested for the production of food.

11. The method according to claim 5, wherein the triglycerides are used as feed for animals, reducing the need for plant-based feed when raising animals.

12. The method according to claim 3, further including a step of adding glycerol and esterifying said free fatty acids to triglycerides.

13. The method according to claim 3, wherein oxygen produced in the electrolysis step is led into a combustion unit for the combustion of organic matter, and carbon dioxide is captured/recovered from flue gases from said combustion.

14. The method according to claim 3, wherein the free fatty acids as such, or after esterification to triglycerides, are formulated into food for human consumption.

15. The method according to claim 3, wherein the free fatty acids as such, or after esterification to triglycerides, are formulated into feed for animal consumption.

16. The method according to claim 3, wherein the free fatty acids as such, or after esterification to triglycerides, are added to culture media for the growing of cells, said cells chosen from yeast cells, bacterial cells, fungal cells, plant cells or non-human animal cells.

17. The method according to claim 12, wherein the triglycerides are used as feed for insects, and said insects are harvested for the production of food.

18. The method according to claim 12, wherein the triglycerides are used as feed for animals, reducing the need for plant-based feed when raising animals.

\* \* \* \* \*